Figure 1:
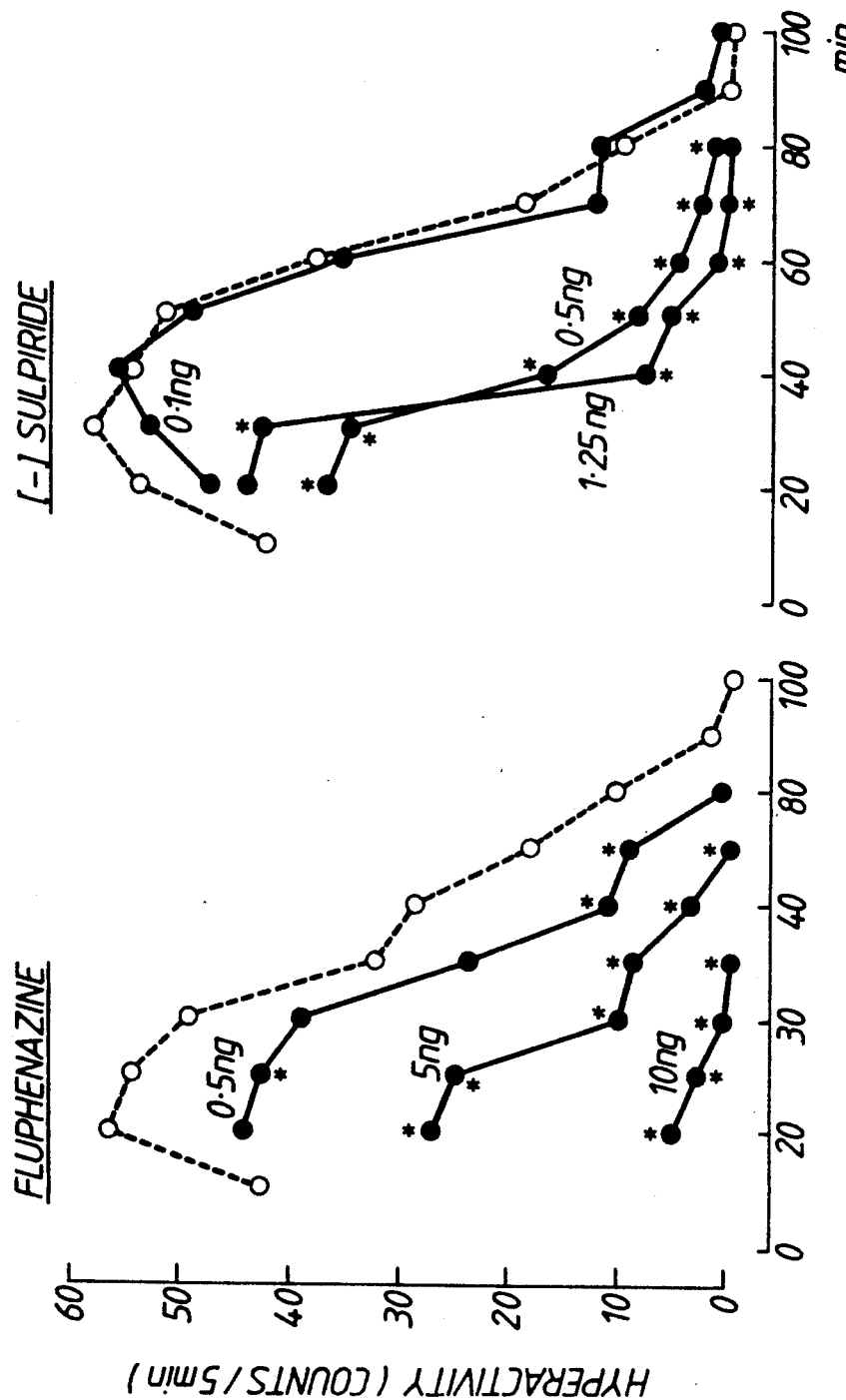

United States Patent [19]

Naylor et al.

[11] Patent Number: 5,025,022
[45] Date of Patent: Jun. 18, 1991

[54] METHOD OF TREATING OR PREVENTING SCHIZOPHRENIA AND/OR PSYCHOSIS USING S-N-(1-AZABICYCLO[2.2.2]OCT-3-YL)BENZAMIDES AND THIOBENZAMIDES

[76] Inventors: Robert J. Naylor; Brenda Naylor, both of The Old Rectory, Addingham, Ilkley, West Yorkshire, LS29 0QP, Great Britain; Alain Renaud, 16, Place des Arts, 92500 Rueil Malmaison; Michel Langlois, 4, Place Cesar Franck, 78530 Buc, both of France

[21] Appl. No.: 389,364
[22] Filed: Aug. 3, 1989
[30] Foreign Application Priority Data Aug. 4, 1988 [EP] European Pat. Off. ......... 88402042.1

[51] Int. Cl.$^5$ .................. A61K 31/44; A61K 31/495; A61K 31/50
[52] U.S. Cl. ................................. 514/305; 514/253
[58] Field of Search ............................. 514/305, 253

[56] References Cited

U.S. PATENT DOCUMENTS

| | | | |
|---|---|---|---|
| 4,657,911 | 4/1987 | Imbert et al. | 514/272 |
| 4,725,603 | 2/1988 | Sanger et al. | 514/306 |
| 4,797,387 | 1/1989 | King | 514/212 |
| 4,857,517 | 8/1989 | Youssefyeh et al. | 514/161 |
| 4,877,794 | 10/1989 | Naylor et al. | 514/305 |
| 4,908,370 | 3/1990 | Naylor et al. | 514/305 |

FOREIGN PATENT DOCUMENTS 0272052  6/1988  European Pat. Off. .

OTHER PUBLICATIONS

Smith et al, Zacopride, a Potent 5-HT$_3$ Antagonist, J. Pharm. Pharmacol. 1988, 40: 301, 302, Nov. 13, 1987.
Drug Treatment of Psychoses, Goodman and Gilman's The Pharmacological Basis of Therapeutics, Sev. Ed. pp. 408–411, (1985).

*Primary Examiner*—Glennon H. Hollrah
*Assistant Examiner*—Gary Hollinden

[57] ABSTRACT

Compounds of general formula I

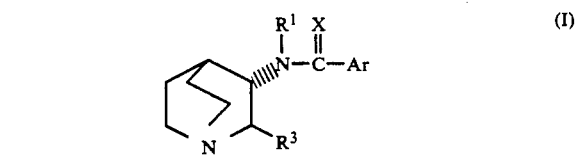

wherein:
X represents oxygen or sulphur;
each of $R^1$ and $R^3$ independently represents hydrogen or a $C_1$-$C_4$ alkyl group;
Ar represents:
a phenyl ring optionally substituted by one, two or three $C_1$-$C_4$ alkoxy groups and/or by one or two halogen atoms; a phenyl ring of the general formula

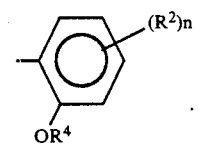

wherein $R^2$ represents halogen, 4,5-benzo, $C_1$-$C_8$ alkoxy, $C_1$-$C_4$ alkylcarbonyl or Am, wherein Am represents amino, methylamino or dimethylamino, $R^4$ represents $C_1$-$C_8$ alkyl,
n is 1 or 2; or
a pyrimidinyl moiety of the general formula

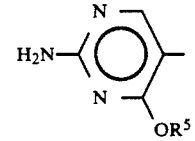

wherein $R^5$ is $C_1$-$C_4$ alkyl;
and their N-oxides and pharmaceutically acceptable salts are useful as antischizophrenic and/or antipsychotic agents. A preferred compound is S(−)-4-amino-N-(1-azabicyclo[2.2.2]oct-3-yl)-5-chloro-2-methoxybenzamide.

4 Claims, 2 Drawing Sheets

METHOD OF TREATING OR PREVENTING SCHIZOPHRENIA AND/OR PSYCHOSIS USING S-N-(1-AZABICYCLO[2.2.2]OCT-3-YL)BENZAMIDES AND THIOBENZAMIDES

The present invention relates to the use of certain optical isomers of N-(3-quinuclidinyl)benzamides and thiobenzamides, namely S-N-(3-quinuclidinyl)-benzamides and thiobenzamides, otherwise known as S-N-(1-azabicyclo[2.2.2]oct-3-yl)-benzamides and thiobenzamides, which have been observed to exhibit antischizophrenic and/or antipsychotic properties in warm blooded animals.

Quinuclidine analogues of sulpiride were prepared and studied by Mikhlina, E. E. et al as reported in *Khim-Farmatsevt. Zh.* 10, No. 11, 56–60 (1976); C.A. 85: 155489r exemplified by the compound: 5-aminosulphonyl-N-(1-azabicyclo[2.2.2]oct-3-yl)-2-methoxybenzamide This compound and others in the series were reported by the authors not to have antiemetic activity. The above named compound was reported in USSR Patent SU-A-414261 to have neuroleptic activity.

Syntheses of 4-amino-N-(1-azabicyclo[2.2.2]oct-3-yl)benzamide and N-(1-azabicyclo[2.2.2]oct-3-yl)benzamide were reported by Mikhlina, E. E. et al in *Khim-Farmatsevt. Zh.* 7, 20–24 (1974); C.A. 79, 146458a and the latter in *Khim.Geterosikl. Soedin., Akad. Nauk. Latv. SSR* 243–9 (1966); C.A. 65: 2220b. These compounds were reported to exhibit hypotensive, narcotic and ganglionic stimulation and blocking activities.

Synthesis of 4-amino-N-(1-azabicyclo[2.2.2]oct-3-yl)-3-chloro-5-trifluoromethylbenzamide was reported in DE-A-2548968; C.A. 87, 68001c and in equivalently related U.S. Pat. No. 4,093,734 from 4-amino-3-chloro-5-trifluoromethyl benzoic acid chloride and 3-aminoquinuclidine. The compound is in a class among pyrrolidinyl and piperidinyl benzamides which are said to be useful as anxiolytics, anticonvulsives, antiemetics and antiulcerogenics.

It is widely recognized that substituted benzamides are a class of drugs known to be effective in psychiatry and gastroenterology (Sulpiride and other Benzamides; International Workshop on Sulpiride and other benzamides, Florence, Feb. 17-18 (1978), Raven Press]. However, the S-N-(1-azabicyclo[2.2.2]oct-3-yl)-benzamides used in this invention have now been found to have marked antischizophrenic properties.

EP-A-0099789 and FR-A-2529548 disclose racemic mixtures of N-(1-azabicyclo[2.2.2]oct-3-yl) benzamides and their use as gastrointestinal motility accelerators.

U.S. Pat. No. 4,593,034 and EP-A-0158532 disclose the treatment of emesis caused by the administration of platinum anticancer drugs (such as cisplatin) by the use of racemic mixtures of 2-alkoxy-N-(1-azabicyclo[2.2.2]oct-3-yl) benzamides or thiobenzamides.

EP-A-0201165 describes a large class of compounds, covering certain racemic mixtures of N-(1-azabicyclo[2.2.2]oct-3-yl) benzamides and reports that they are useful in the treatment of emesis, anxiety and/or irritable bowel syndrome (IBS).

EP-A-0190920 discloses the enhancement of memory or the treatment of memory deficiency by the administration of certain racemic mixtures of arylamido- and arylthioamido-azabicycloalkanes including racemic mixtures of N-(1-azabicyclo[2.2.2]oct-3-yl) benzamides.

GB-A-2193633 discloses a large class of compounds, including N-(1-azabicyclo[2.2.2]oct-3-yl) benzamides for the treatment of stress-related psychiatric disorders, for increasing vigilance, for the treatment of rhinitis or serotonin-induced disorders, for increasing the bioavailability of other active agents and for nasal administration.

EP-A-0280603 (published 31st Aug. 1988) discloses that S-enantiomers of the compounds disclosed in EP-A-0099789 increase the motility of certain areas of the gastrointestinal tract and inhibit emesis, particularly that induced by cisplatin.

EP-A-0311724 (published 19th Apr. 1988) discloses that R-enantiomers of N-(1-azabicyclo[2.2.2]oct-3-yl) benzamides have anxiolytic activity.

It has now unexpectedly been discovered that the S-enantiomers of various N-(1-azabicyclo[2.2.2]oct-3-yl)benzamides exhibit antischizophrenic and/or antipsychotic activity in warm blooded animals.

According to the present invention, there is provided the use of a compound of general formula I

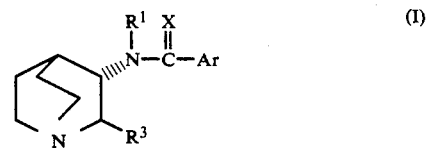

wherein:
X represents oxygen or sulphur;
each of $R^1$ and $R^3$ independently represents hydrogen or a $C_1$–$C_4$ alkyl group;
Ar represents:
a phenyl ring optionally substituted by one, two or three $C_1$–$C_4$ alkoxy groups and/or by one or two halogen atoms; a phenyl ring of the general formula

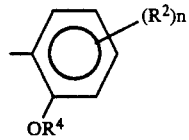

wherein $R^2$ represents halogen, 4,5-benzo, $C_1$–$C_8$ alkoxy, $C_1$–$C_4$ alkylcarbonyl or Am, wherein Am represents amino, methylamino or dimethylamino, $R^4$ represents $C_1$–$C_8$ alkyl,
n is 1 or 2; or a pyrimidinyl moiety of the general formula

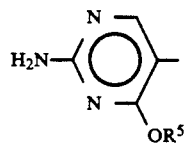

wherein $R^5$ is $C_1$–$C_4$ alkyl;
or an N-oxide and/or pharmaceutically acceptable salt thereof,
in the preparation of an antischizophrenic and/or antipsychotic agent.

The compound will generally be substantially free of the R-enantiomer.

Preferred compounds useful in the invention include those having one or more of the following features:

each of $R^1$ and $R^3$ independently represents hydrogen, methyl or ethyl

Ar represents 4-Am-5-chloro-2-methoxyphenyl.

A particularly preferred compound useful in the invention is S-(+)-4-amino-N-(1-azabicyclo[2.2.2]oct-3-yl)-5-chloro-2-methoxybenzamide whether as the free base or a salt (for example fumarate or hydrochloride).

In the further definition of symbols in the formulae hereof and where they appear elsewhere throughout this specification and the claims, terms have the following significance.

The term "$C_1$–$C_8$alkyl" as used herein includes straight and branched chain radicals of up to eight carbons inclusive and is exemplified by such groups as methyl, ethyl, propyl, isopropyl, butyl, amyl, hexyl, heptyl, and octyl radicals and the like. The term "$C_1$–$C_8$ alkoxyl" has the formula —O—$C_1$–$C_8$alkyl. The terms "$C_1$–$C_4$alkyl" and "$C_1$–$C_4$alkoxyl" are to be construed as containing up to four carbon atoms accordingly.

The terms "halo" or "halogen" when referred to herein include fluorine, chlorine, bromine and iodine unless otherwise stated. Chlorine and bromine are preferred. "Pharmaceutically acceptable salts" include the acid addition salts, hydrates, alcoholates and salts of the compounds, which salts are physiologically compatible in warm blooded animals. The acid addition salts may be formed by either strong or weak acids. Representative of strong acids are hydrochloric, sulphuric and phosphoric acids. Representative of weak acids are fumaric, maleic, succinic, oxalic, citric, tartaric, cyclohexamic and the like.

Protected amino groups used in synthesis are acetylamino or benzoylamino radicals and the like on the benzamide moiety mentioned hereinbelow in synthetic methods.

The optically active compounds (which term includes salts where the context so admits) useful in the invention may broadly speaking be prepared either by separation from racemates or other mixtures with the corresponding R-enantiomer or by asymmetric synthesis, as in EP-A0-87402321.1.

A process for the preparation of a compound of general formula I therefore comprises either (1) separating a compound of general formula I from a mixture with its corresponding R-enantiomer; or (2 1.1) coupling a 3-aminoquinuclidine of absolute configuration S of general formula (II)

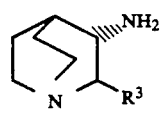

wherein $R^3$ is as defined for general formula (I) with an acid of general formula (III):

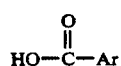

wherein Ar is as defined for general formula (I); or (2.1.2) reacting an S-3-aminoquinuclidine of general formula (II) with an acid derivative of general formula (IIIa)

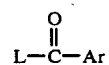

wherein Ar is as defined for general formula (I) and L is a leaving group; and (2.1.3) optionally after step 2.1.1 or 2.1.2 converting a compound of general formula (I) so formed in which X represents an oxygen atom into a compound of general formula (I) in which X represents a sulphur atom; or (2.2) when X represents a sulphur atom reacting an S-3-aminoquinuclidine of general formula (II) with an aldehyde ArCHO wherein Ar is as defined for general formula (I) and sulphur; or (2.3) for an amino-substituted compound of general formula (I) reducing a corresponding nitro-substituted compound, and (2.4) optionally after any of steps 1, 2.1.1, 2.1.2, 2.1.3, 2.2 and 2.3 converting a compound of general formula (I) so formed into another compound of general formula (I) or an N-oxide and/or salt thereof.

N-oxides can be prepared by treatment with a peracid such as m-chloroperbenzoic acid or hydrogen peroxide in an organic solvent such as methylene chloride at room temperature. Salts can be prepared as described above.

Process (1) may be achieved for example by recrystallisation of a salt formed with an optically active acid (for example an enantiomer of tartaric acid). By way of illustration, the following protocol may be followed for the resolution of N-(3-quinuclidinyl)-3-chlorobenzamide (N-(1-azabicyclo[2.2.2]oct-3-yl)-3-chlorobenzamide).

To the racemate in base form is added a solution of dextrorotatory L tartaric acid in methanol. The mixture obtained is brought to reflux, filtered when hot and left to cool. The precipitate is filtered and redissolved in boiling methanol. After cooling and filtration, the precipitate is dissolved in boiling methanol again. After cooling and filtration, the compound obtained is dissolved in water; the resulting aqueous solution is basified by means of sodium carbonate, extracted with chloroform, dried on sodium sulphate and filtered. The filtrate is evaporated. The product obtained is dissolved in acetone and hydrochloric ethanol (about 6N) is added; the precipitate obtained is filtered and recrystallized in ethanol. Thus, the dextrorotatory isomer is obtained.

The mother liquor of the first three recrystallizations in methanol and combined and evaporated. The residue is taken in water, and the resulting mixture is basified by means of sodium carbonate and then extracted with chloroform. The extract is dried on sodium or magnesium sulphate and filtered. The filtrate is evaporated. To the product is added a solution of laevorotatory D-tartaric acid in methanol. The mixture is brought to reflux, filtered when hot and the filtrate is cooled. The precipitate obtained is then filtered. This precipitate is dissolved in boiling methanol and the solution is filtered when hot. After the filtrate has cooled, the precipitate obtained is filtered. A precipitate is obtained which is dissolved in water. The solution is basified by means of sodium carbonate, extracted with chloroform and the extract is dried on sodium or magnesium sulphate. It is then filtered and the filtrate is then evaporated leaving a residue which is dissolved in acetone and hydrochloric ethanol (about 6N). The precipitate obtained is filtered and recrystallized in ethanol. In this way, the laevorotatory isomer is obtained.

PREPARATION OF BENZAMIDES

Racemates of compounds of Formula I and the corresponding R- or S-isomers are preparable by reacting a suitably activated benzoic acid derivative with 3-aminoquinuclidine to form the corresponding benzamide under a variety of conditions. Two general methods, A and B, are illustrated in the following equations:

Method A, Using an Acid Chloride

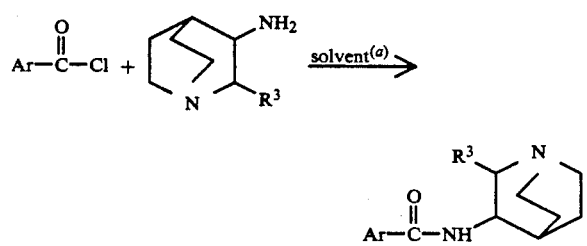

(a) Suitable solvents are organic solvents or a mixture of organic solvents and water; examples of organic solvents include chloroform and diethyl ether.

Method A is illustrated by Examples 5, 6, 7 and 9.

Method B, Using a Coupling Agent

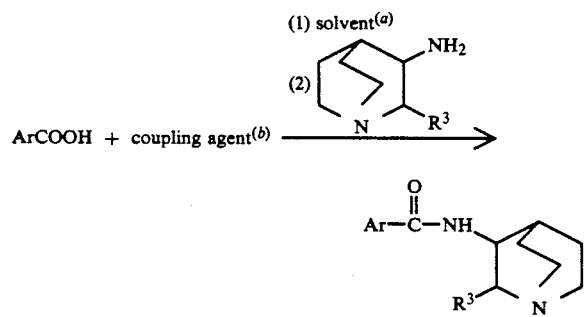

(a) e.g., tetrahydrofuran
(b) e.g., dicyclohexylcarbodiimide or 1,1'-carbonyldiimidazole Method B is illustrated in Examples 1, 3 and 8 and 14.

Compounds wherein $R_2$ is primary amino may also be prepared from a compound prepared by Methods A or B, wherein $R_2$ is nitro by catalytic reduction of the nitro compound.

Alternatively, compounds wherein $R_2$ is amino may be prepared by procedures of Method A utilizing a starting benzoyl halide wherein the amino group has been protected, or they may be prepared from compounds prepared in Method A or B wherein $R_2$ is nitro and reducing the nitro radical to an amino radical.

Preferably, the compounds wherein $R_2$ is amino or methylamino are prepared by Method B.

The free base of any compound of Formula I from its acid addition salt may be regenerated by usual procedures of partitioning between dilute aqueous base and a suitable solvent, separating the solvent layer, drying and evaporating.

Preparation of Thiobenzamides

The preparation of the thiobenzamido compounds of Formula I' may be accomplished by mixing and reacting a benzamido compound of Formula I with a mixture of phosphorus pentasulphide ($P_2S_5$) and potassium sulphide ($K_2S$) or by mixing and reacting 3-aminoquinuclidine with an appropriately substituted benzaldehyde and sulphur. The reaction sequences are illustrated by the following:

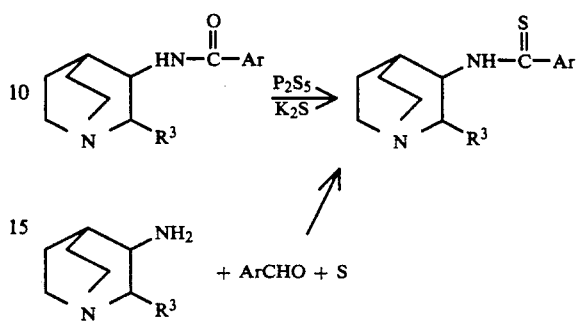

In these methods, compounds wherein $R_2$ is nitro may be reduced to compounds wherein $R_2$ is amino.

A preferred group of compounds encompassed by Formula I have the formula:

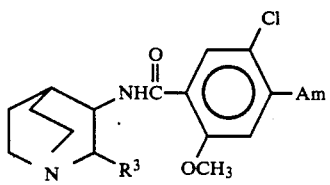

wherein Am is amino (i.e., —$NH_2$) or methylamino. As will be recognized from the above description, these compounds (Ic) are preferably prepared by Method B.

In process step 2.1.1 the coupling may be effected by means of a carbodiimide such as dicyclohexylcarbodiimide or 1,1'-carbonyldiimidazole.

In process step 2.1.2 the leaving group L may be a halogen atom (such as chlorine) in which case the compound of general formula (IIIa) will be an acid halide.

In process step 2.1.3 the conversion of a compound of general formula (I) where X is an oxygen atom to a compound of general formula (I) where X is a sulphur atom may be effected by mixing and reacting with a mixture of phosphorus pentasulphide and potassium sulphide.

An S-3-aminoquinuclidine of general formula (II) may be prepared by a number of different ways as follows. Although the following description is given primarily with reference to the case when $R^3$ is hydrogen (that is, when the 3-aminoquinuclidine moiety is otherwise unsubstituted), it is to be understood that it is equally applicable to cases where $R^3$ is an alkyl radical. Compounds of general formula (II) can be prepared by the reduction of the oxime of the corresponding 3-quinuclidinone by treatment with hydrogen and Raney nickel. The oximes in turn are preparable by treatment of the corresponding 3-quinuclidinones with hydroxylamine hydrochloride in the presence of base. The 2-alkyl-3-quinuclidinones can be prepared by reduction with palladium-on-carbon; their production is described in J. Het. Chem. 3 109 (1966).

First, a compound of general formula (II) may be obtained by hydrolysing an optionally substituted benzamide such as an S-N-(3-quinuclidinyl)-3-chlorobenzamide of general formula (IV):

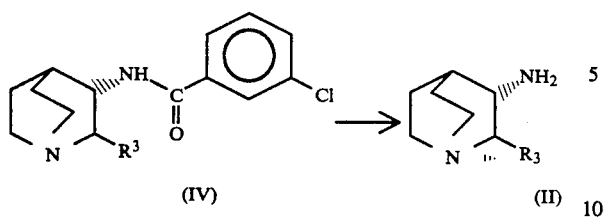

Hydrolysis may be achieved by dilute acid, such as dilute hydrochloric acid, in which case the dihydrochloride salt of compound (II) will result.

S-N-(3-quinuclidinyl)-3-chlorobenzamides of general formula (IV) may be separated from a racemic mixture by crystallization of the diastereoisomeric salts obtained by the action of L-tartaric acid. Treatment of the appropriately separated salt with base yields the free S-N-(3-quinuclidinyl)-3-chlorobenzamide.

A racemic mixture of R- and S-N-(3-quinuclidinyl)-3-chlorobenzamides may be obtained by condensing a racemic 3-aminoquinuclidine with a reactive derivative of 3-chlorobenzoic acid or with 3-chlorobenzoic acid itself and a coupling agent such as a carbodiimide. Racemic 3-aminoquinuclidines may be obtained by the action of hydroxylamine or hydrochloride followed by base (such as sodium ethoxide) on 3-quinuclidinones and reduction of the corresponding oxime with hydrogen and Raney nickel, as an example. If necessary 3-quinuclidinones may be prepared by oxidising 3-quinuclidinols, whose preparation is described in *J. Am. Chem. Soc* 74, 2215 (1952).

Secondly, a compound of general formula (II) may be produced by debenzylating R-N-(alpha-methylbenzyl)-S-3-aminoquinuclidine by hydrogenolysis in an acid medium in the presence of a catalyst such as palladium on carbon.

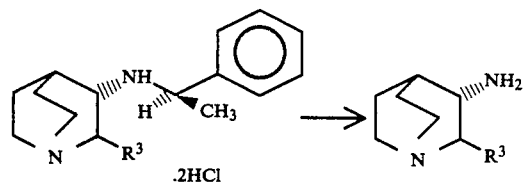

R-N-(alpha-methylbenzyl)-S-3-aminoquinuclidine may be obtained by the reduction of R-N-(alpha-methylbenzyl)-3-quinuclidinimine by hydrogenolysis in the presence of a catalyst such as platinum oxide or by a borohydride such as potassium borohydride.

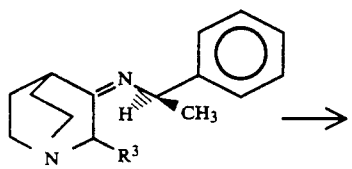

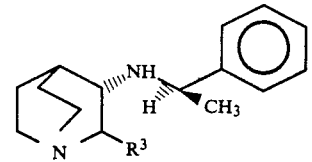

In turn, the R-N-(alpha-methylbenzyl)-3-quinuclidinimine may be obtained by treating 3-quinuclidinone with R-alpha-methylbenzylamine.

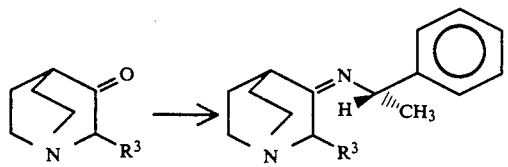

A compound of general formula I may therefore be used in pharmaceutical and/or veterinary medicine, in the treatment or prophylaxis of schizophrenia and/or psychoses.

Compounds of general formula I will frequently be used in a pharmaceutical and/or veterinary composition comprising (a) a compound of general formula I and (b) a suitable carrier therefor.

The antischizophrenic activity was determined by the method of Costall et al details of which are to be found in the pharmacology examples later in this specification. In brief, the method involves seeing whether the compound under test antagonises the response of the rat to intracerebrally injected amphetamine.

It is therefore a primary object to provide a method of treating schizophrenia and/or psychosis by the administration of an effective dose of certain S-N-(1-azabicyclo[2.2.2]oct-3-yl)benzamides and thiobenzamides.

A still further object is to provide means for treating schizophrenia and/or psychosis.

The invention will now be illustrated by the following non-limiting examples.

EXAMPLE 1

S(-)-4-Amino-N-(1-azabicyclo[2.2.2]oct-3-yl)-5-chloro-2-methoxybenzamide, fumarate 1:1]

(S(-)-4-Amino-5-chloro-2-methoxy-N-(quinuclidin-3-yl)benzamide, fumarate [1:1])

In a closed system equipped with an oil bubbler, 30 ml of tetrahydrofuran was added to a mixture of 4-amino-5-chloro-2-methoxybenzoic acid, 2.02 g, (0.010 mole) and 1,1'-carbonyldiimidazole, 1.62 g (0.010 mole) with stirring. When evolution of carbon dioxide ceased, nitrogen was bubbled through the reaction mixture for 1 hr. A solution of 3-aminoquinuclidine, 1.26 g, (0.010 mole) in 10 ml tetrahydrofuran was added dropwise to the stirred reaction mixture and stirring at room temperature continued for 3 hrs. TLC analysis (3% conc. ammonium hydroxide solution in methanol) showed some product formation. The mixture was heated at reflux temperature for 18 hours and then concentrated to an oil. TLC analysis showed the presence of the product, imidazole, and 3-aminoquinuclidine. The oil was dissolved in methylene chloride (75 ml) and washed twice with 50 ml protions of aqueous sodium bicarbonate solution. The methylene chloride layer was dried over anhydrous magnesium sulphate and concentrated to yield 2.0 g (67%) of a glassy amorphous solid, the free base of the title compound.

In another reaction on a 0.020 mole scale, 5.18 g (83.8%) of the product as the free base was obtained.

The products were combined, dissolved in methanol (20 ml) and the solution and treated with a solution of fumaric acid (2.73 g) in methanol (50 ml). Absolute ether was added to precipitate the salt which was collected by filtration and recrystallized from methanol-water (200:20) with isopropyl ether added to the point of incipient cloudiness. The recrystallized salt (5.38 g) melted at 223°-225° C.

Analysis: Calculated for $C_{19}H_{24}N_3O_6Cl$: C,53.59; H,5.68; N,9.89. Found: C,53.35; H,5.72; N,9.95.

From the racemate, the R(+) isomer and the S(-) isomer are separated.

EXAMPLE 2

S(-)-4-Amino-N-(1-azabicyclo[2.2.2]oct-3-yl)-5-chloro-2-methoxybenzamide, hydrochloride, hydrate (1:1:1)

(S(-)-4-Amino-5-chloro-2-methoxy-N-(quinuclidin-3-ylbenzamide, hydrochloride, hydrate (1:1:1))

To an isopropyl alcohol solution of the free base of the title compound such as was obtained by the procedure of Example 1 is added an equal molar amount of 37% (conc.) hydrochloric acid. The crude salt is separated by filtration and recrystallized from acetone-water to give the title compound, m.p. 158°-160° C. From the racemate, the S(-) isomer is separated.

EXAMPLE 3

S-N-(1-Azabicyclo[2.2.2]oct-3-yl)-5-chloro-2-methoxy-4-(methylamino)benzamide, fumarate [1:1]

(S-5-chloro-2-methoxy-4-methylamino-N-(quinuclidin-3-yl)benzamide, fumarate [1:1])

To a mixture of 1,1'-carbonyldiimidazole, 1.23 g (0.00756 mole) and 5-chloro-2-methoxy-4-methylaminobenzoic acid, 1.63 g (0.00756 mole) was added 50 ml of tetrahydrofuran. Nitrogen was bubbled into the solution for 30 minutes to remove any carbon dioxide that was present. To the solution was added 3-aminoquinuclidine, 0.95 g, (0.00756 mole) in one portion, and the reaction mixture was stirred at ambient temperature for 16 hours. The reaction mixture was concentrated to an oil which was shown to be 1:1 mixture of the free base of the product and imidazole. The mixture was dissolved in 20 ml methanol and treated with a solution containing 0.47 g fumaric acid in 20 ml of hot methanol. Upon cooling, 1.52 g of white solid formed. Recrystallization from water-methanol gave 0.84 g of the product as a white solid; m.p. 237°-238° C.

Analysis: Calcuated for $C_{20}H_{26}N_3O_6Cl$: C,54.61; H,5.96; N,9.55 Found: C,54.61; H,5.98; N,9.51.

From the racemate, the S isomer is separated.

EXAMPLE 4

S-N-(1-Azabicyclo[2.2.2]oct-3-yl)-5-chloro-2-methoxy-4-(methylamino)-benzamide, hydrochloride (1:1)

(S-5-chloro-2-methoxy-4-(methylamino)-N-(quinuclidin-3-yl)benzamide, hydrochloride (1:1)

To an isopropyl alcohol solution of the free base of the title compound, such as was obtained by the procedure of Example 3, is added an equal molar amount of 37% (conc.) hydrochloric acid. The crude salt is separated by filtration and recrystallized from ethanol-water to give the title compound, m.p. 255°-258° C. From the racemate, the S isomer is separated.

EXAMPLE 5

S-N-(1-Azabicyclo[2.2.2]oct-3-yl)-2-methoxybenzamide, fumarate [1:1]hemihydrate (S-2-methoxy-N-(quinuclidin-3-yl)benzamide, fumarate [1:1]hemihydrate).

In a closed system equipped with an oil bubbler, a solution of 2-methoxybenzoyl chloride, 2.76 g (0.0016 mole) in 50 ml absolute ether was added dropwise over 10 min to a stirred solution of 3-aminoquinuclidine, 1.81 g (0.0144 mole) in 100 ml absolute ether. After the addition was completed, the mixture was stirred at room temperature for an additional 2 hrs. The solid hydrochloride salt was collected by filtration under nitrogen. The salt (3.83 g) was dissolved in sodium bicarbonate solution and extracted twice with 25 ml portions of methylene chloride. The extract was dried over magnesium sulphate and concentrated to yield 1.25 g clear oil (33.3%). TLC analysis (3% conc. ammonium hydroxide in methanol) showed the free base to be pure. A solution of 1.17 g of the free base in 5 ml methanol was treated with a solution of 0.52 g fumaric acid in 10 ml methanol. Isopropyl ether was added to give approximately 100 ml of solution from which the fumarate salt precipitated. The salt was collected under nitrogen and dried in a vacuum oven at 60° C. overnight. NMR and elemental analyses showed that the product was a hemihydrate.

Analysis: Calculated for $C_{19}H_{25}N_2O_{6.5}$: C,59.21; H,6.54; N,7.27. Found: C,59.18; H,6.30, N,7.25.

From the racemate, the S isomer is separated.

EXAMPLE 6

S-N-(1-Azabicyclo[2.2.2]oct-3-yl)-2,4-dimethoxybenzamide hydrochloride [1:1]

(S-N-(quinuclidinyl-3-yl)-2,4-dimethoxybenzamide hydrochloride [1:1]

A mixture of 3-aminoquinuclidine dihydrochloride, 6.95 g, (0.0349), 2,4-dimethoxybenzoyl chloride, 700 g, (0.0349 mole), anhydrous sodium carbonate, 36.99 g, (0.349 mile), 175 ml water, and 175 ml chloroform was stirred rapidly to achieve good mixing of the 2 layers for 20 hrs. The chloroform layer was then separated, washed with water, dried over anhydrous magnesium sulphate, and concentrated to an impure oil. The oil was triturated twice with 20 ml portions of petroleum ether to remove some impurities. The oil was then dissolved in ether and filtered to remove a small amount of insoluble material. The filtrate was treated with ethereal hydrogen chloride and the resulting salt collected to yield 2.70 g (23.7% yield) white solid. The salt was recrystallized from ethanol-isopropyl ether. Further recrystallization from methanol-ethyl ether yielded a white solid, m.p. 211°-212° C. The NMR analysis was satisfactory.

Analysis: Calculated for $C_{16}H_{23}N_2O_3Cl$: C,58.80; H,7.09; N,8.57 Found: C,58.38; H,7.13; N,8.44.

From the racemate, the S isomer is separated.

EXAMPLE 7

S-N-(1-Azabicyclo[2.2.2]oct-3-yl)-2,4-dimethoxybenzamide, sulphate[1:]

(S-2,4-dimethoxy-N-(quinuclidin-3-yl)benzamide, sulphate[1:])

In a closed system equipped with an oil bubbler, a solution of 2,4-dimethoxybenzoyl chloride, 13.08 g, (0.0652 mole) in 200 ml absolute ether was added dropwise over 30 minutes to a stirred solution of 3-aminoquinuclidine, 7.80 g, (0.0619 mole) in 200 ml absolute ether. The mixture was stirred overnight, and the solid hydrochloride salt of the product was filtered under nitrogen. The material was dried in a vacuum oven at 40° C. to give 18.70 g (92%). A 2.94 g (0.009 mole) portion of the hydrochloride salt in 20 ml methanol was treated with a solution of sodium methoxide prepared from 0.23 g (0.010 mole) sodium metal and 10 ml methanol. After standing a few minutes, the mixture was filtered and the filtrate concentrated on a rotary evaporator, and the residue was triturated with 75 ml methylene chloride. After filtering to remove some insoluble solids, the filtrate was concentrated to yield 2.53 g of the free base of the title compound (97% recovery from the hydrochloride salt). The free base was dissolved in 100 ml acetone and concentrated sulphuric acid (0.483 ml) added dropwise with stirring. The solid that formed was collected under nitrogen to give 2.76 g of the salt which recrystallized from methanol-isopropyl ether and dried in a vacuum oven at 60° C. for 2 hrs and then overnight at 78° C.; m.p. 223°–225° C.

Analysis: Calculated for $C_{16}H_{24}N_2O_7S$: C,49.47; H,6.23; N,7.23. Found: C,49.41; H,6.30; N,7.25.

From the racemate, the S isomer is separated.

EXAMPLE 8

S-N-(1-Azabicyclo[2.2.2]oct-3-yl)-2,4-dimethoxybenzamide, fumarate [1:1.5]

(S-2,4-dimethoxy-N-(quinuclidin-3-yl)benzamide, fumarate 1:1.5])

In a closed system equipped with an oil bubbler, tetrahydrofuran, 100 ml, was added to a mixture of 2,4-dimethoxybenzoic acid, 3.64 g (0.020 mole) and 1,1'-carbonyldiimidazole, 3.24 g (0.020 mole). No evolution of carbon dioxide was observed and after stirring for 3 hrs, TLC (ethyl acetate) and mass spectral analysis showed that the starting material had reacted to form N-(2,4-dimethoxybenzoyl)imidazole and imidazole. A solution of 3-aminoquinuclidine, 2.52 g (0.020 mole) in 10 ml tetrahydrofuran was added to the mixture, and the solution was heated to reflux temperature for 1 hr and then allowed to stand overnight at room temperature. A solution of fumaric acid, 2.32 g (0.020 mole) in 50 ml methanol was added to the reaction mixture. Tetrahydrofuran was added until the solution became slightly turbid. The solution was chilled in a refrigerator. The solid which precipitated from solution was collected by filtration and found to be a fumarate salt of 3-aminoquinuclidine. The filtrate was concentrated to an oil and triturated with tetrahydrofuran. The solid precipitate which formed on standing was filtered and shown by TLC (3% concentrated ammonium hydroxide in methanol) to be the desired product plus traces of imidazole and 3-aminoquinuclidine. Recrystallization from methanolisopropyl ether gave 5.41 g white crystalline solid (67% yield calculated as the monofumarate). NMR and elemental analysis showed the salt to contain less than one equivalent of fumaric acid. The salt was dissolved in boiling methanol (50 ml) and treated with an additional 0.77 g (0.0066 mole) fumaric acid in 10 ml hot methanol. Isopropyl ether was added until the hot solution became turbid. The solid obtained on cooling was collected, recrystallized from methanol-isopropyl ether and dried in a vacuum oven at 78° C. overnight. NMR and elemental analysis showed the salt to be a 1.5 fumarate, m.p. 192°–192.5° C.

Analysis: Calculated for $C_{22}H_{28}N_2O_9$: C,56.89; H,6.08; N,6.03. Found: C,56.81; H,6.13; N,6.04.

From the racemate, the S isomer is separated.

EXAMPLE 9

S-N-(1-Azabicyclo[2.2.2]oct-3-yl)-2-propoxybenzamide hydrochloride [1:1]

(S-2-propoxy-N-(quinuclidin-3-yl)benzamide hydrochloride [1:1])

To a solution of 3.82 g (0.0192 mole) of 3-aminoquinuclidine dihydrochloride in about 25 ml of carbon dioxide-free water was added 8 g (0.025 mole) of barium hydroxide octahydrate. The mixture was warmed for 5 minutes and then dried to a powder on a rotary evaporator. While protecting from contamination with carbon dioxide in the atmosphere, the powder was extracted in sequence with hot benzene and a 1:1 mixture of benzene-methylene chloride solution. The combined extracts were dried over magnesium sulphate and the mixture filtered. To the filtrate with agitation was added dropwise a solution of 3.4 g (0.0171 mole) of 2-propoxybenzoyl chloride in 50 ml of methylene chloride. The mixture was warmed on a steam bath to evaporate about 75% of the methylene chloride. Ligroin (60–110) was added and the mixture solidified. The solid was recrystallized from anhydrous ethyl alcohol to give 3.9 g (62.0%), m.p. 210°–211° C.

Analysis: Calculated for $C_{17}H_{25}N_2O_2Cl$: C,62.86; H,7.75; N,8.62. Found: C,62.62; H,7.59; N,8.54.

From the racemate, the S isomer is separated.

EXAMPLE 10

S-N-(1-Azabicyclo[2.2.2]oct-3-yl)-3-methoxy-2-naphthalene-carboxamide, hydrochloride [1:1]

(S-3-methoxy-2-naphthalene-N-(quinuclidin-3-yl)carboxamide, hydrochloride [1:1])

A solution of 1.69 g (0.00768 mole) of 3-methoxy-2-naphthoic acid chloride in 15 ml of methylene chloride was added dropwise to a stirred solution of 0.97 g (0.00768 mole) of 3-aminoquinuclidine in 25 ml of methylene chloride in a closed system equipped with an oil bubbler. The reaction mixture was stirred overnight at ambient temperature, and then concentrated to give an off-white glassy solid. Two recrystallizations from methanol-isopropyl ether gave 1.95 g (73.4%) of the product as an off-white solid which was vacuum dried at ambient temperature, m.p. 248°–252° C.

analysis: Calculated for $C_{19}H_{23}N_2O_2Cl$: C,65.79; H,6.68; N,8.08. Found: C,65.40; H,6.72; N,8.01.

From the racemate, the S isomer is separated.

EXAMPLE 11

S-4-Amino-N-(1-azabicyclo[2.2.2]oct-3-yl)-5-chloro-2-methoxythiobenzamide fumarate (S-4-Amino-5-chloro-2-methoxy-N-(quinuclidin-3-yl)thiobenzamide fumarate)

One half mole of 4-amino-N-(1-azabicyclo[2.2.2]oct-3-yl)-5-chloro-2-methoxybenzamide fumarate is partitioned between dilute sodium hydroxide and 400 ml of benzene. The benzene solution is dried with sodium sulphate and distilled to a volume of 250 ml. To this is added a finely-ground mixture of 9 g of phosphorous pentasulphide and 9 g of potassium sulphide. The mixture is refluxed for 4 hr and an additional 9 g of phosphorous pentasulphide is added and reflux continued for 2 hr. The benzene is decanted off. The solid is dissolved in a suitable solvent and reacted with fumaric acid to give the title compound. From the racemate the 3-S isomers are separated.

S-4-Amino-N-(1aza-2-methylbicyclo[2.2.2]oct-3-yl)-5-chloro-2-methoxybenzamide, fumarate [1:1]

(S-4-Amino-5-chloro-2-methoxy-N-(2-methylquinuclidin-3-yl)benzamide, fumarate [1:1])

Following the general procedure of Example 1, but instead of the 3-aminoquinuclidine, using 0.010 moles of 3-amino-2-methylquinuclidine, the title compound was prepared. From the racemate, the 3-S isomers were separated.

EXAMPLE 13

S-4-Amino-N-(1-aza-2-methylbicyclo2.2.2]oct-3-yl)-5-chloro-2-methoxybenzamide, hydrochloride, hydrate (1:1:1)

S-4-Amino-5-chloro-2-methoxy-N-(2-methylquinuclidin-3-yl)benzamide, hydrochloride, hydrate (1:1:1)

To an isopropyl alcohol solution of the free base of the title compound such as was obtained by the procedure of Example 1 is added an equal molar amount of 37% (conc.) hydrochloric acid. The crude salt is separated by filtration and recrystallised from acetone-water to give the title compound. From the racemate, the 3-S isomers were separated.

PREPARATION 1

S(-)-3-aminoquinuclidine, dihydrochloride (S(-)-1-azabicyclo2.2.2]oct-3-ylamine, dihydrochloride)

(a) Preparation of S(-)-N-(3-quinuclidinyl)-3-chlorobenzamide, hydrochloride (S(-)-N-(1-azabicyclo[2.2.2]oct-3-yl)-5-chloro-2-methoxybenzamide, hydrochloride)

N-(3-quinuclidinyl)-3-chlorobenzamide (52.5 g) in solution in methanol is added to a solution of D-tartaric acid (29.7 g) in methanol. The precipitate obtained is recovered by filtration and treated twice with methanol at reflux. The salt thus purified is decomposed by an aqueous caustic soda solution and the product extracted with chloroform. After drying and evaporation of the organic phase the base obtained is treated in acetone with an ethanolic hydrochloric acid solution. The hydrochloride which precipitates is recovered by filtration and recrystallised from ethanol. 9.4 g of optically pure S(-)-N-(3-quinuclidinyl)-3-chlorobenzamide, hydrochloride (S(-)-N-(1-azabicyclo[2.2.2]oct-3-yl)-5-chloro-2-methoxybenzamide, hydrochloride) are obtained.

Melting point: 244°–247° C.

$[alpha]_D^{20} = -16.8°$ (1, $CH_3OH$).

(b) Preparation of S(-)-3-aminoquinuclidine, dihydrochloride (S(-)-1-azabicyclo[2.2.2]oct-3-ylamine, dihydrochloride)

The hydrochloride obtained in the preceding step (9 g) is treated with concentrated hydrochloric acid at reflux for 3 hours 30 minutes. The reaction mixture is treated with absolute alcohol and the S(-)-3-aminoquinuclidine, dihydrochloride (S(-)-1-azabicyclo[2.2.2]oct-3-ylamine, dihydrochloride) which crystallises is recovered by filtration.

Melting point: >260° C.

$[alpha]_D^{20} = -24.9°$ (c=1, $H_2O$).

PREPARATION 2

S(-)-3-aminocuinuclidine, dihydrochloride (S(-)-1-azabicyclo2.2.2]oct-3-ylamine, dihydrochloride)

(a) Preparation of R(+)-N-(alpha-methylbenzyl)-3-quinuclidinimine

3-Quinuclidinone (80 g) in 800 ml toluene was refluxed in the presence of R-alpha-methylbenzylamine (77.4 g) for 24 hours, the water formed being eliminated by means of a Dean-Stark trap. The reaction mixture is then concentrated to dryness and the resulting imine (130 g) is distilled.

Yield: 89%.

Boiling point: 140°–150° C. (0.05 mm Hg).

$[alpha]_D^{20} = +97.2°$ (c=1, $CHCl_3$).

(b) Preparation of R-N-(alpha-methylbenzyl)-S-3-aminoquinuclidine, dihydrochloride The imine (129.5 g) obtained in the preceding step is dissolved in methanol and potassium borohydride (30.6 g) is added in small portions at between 10° and 20° C. After one hour the mixture is evaporated to dryness under reduced pressure. The residue is dissolved in a mixture of acetone and isopropyl alcohol (2:1). The expected amine is precipitated in the form of the dihydrochloride by the addition of an ethanolic hydrogen chloride solution. The product is recrystallised twice in an ethanol/methanol mixture (1:1) to yield optically pure R-N-(alpha-methylbenzyl)-S-3-aminoquinuclidine, dihydrochloride (81 g).

Yield: 47%.

Melting point >260° C.

$[alpha]_D^{20} = -2$ (C=2, $H_2O$).

(c) Preparation of S(-)-3-aminoquinuclidine, dihydrochloride (S(-)-1-azabicyclo[2.2.2]oct-3-ylamine, dihydrochloride)

The product obtained in the preceding step (64.4 g) is dissolved in ethanol with 2 equivalents of a solution of hydrochloric acid (1N) and palladium on carbon, 50% $H_2O$ (12.8 g). The reaction mixture is stirred for 18 hours under a hydrogen atmosphere, filtered then evaporated to dryness under reduced pressure. S(-)-3-aminoquinuclidine, dihydrochloride is crystallised in an ethanol:ether (1:1) mixture.

$[alpha]_D^{20} = -24.2$ (1, $H_2O$).

COMPARISON PREPARATION 1

R(+)-3-aminoquinuclidine, dihydrochloride (R(+)-1-azabicyclo[2.2.2]oct-3-ylamine, dihydrochloride)

Following the procedure of Preparation 1, but using instead L-tartaric acid, the corresponding R enantiomer was obtained.

Melting point: >260° C.

[alpha]$_D^{20}$ = +24.8° (c=1, H$_2$O).

COMPARISON PREPARATION 2

R(+)-3-aminoquinuclidine, dihydrochloride (R(+)-1-azabicyclo[2.2.2]oct-3-ylamine, dihydrochloride)

Following the procedure of Preparation 2, but using instead S-N-alpha-methylbenzylamine, the corresponding R enantiomer was obtained.

Melting point >260° C.

[alpha]$_D^{20}$ = +24.4° (c=1, H$_2$O). cEXAMPLE 14

S(-)-4-Amino-N-(3-quinuclidinyl)-5-chloro-2-methoxybenzamide hydrochloride (S(-)-4-Amino-N-(1-azabicyclo[2.2.2]oct-3-yl)-5-chloro-2-methoxybenzamide hydrochloride)

S(-)-3-aminoquinuclidine dihydrochloride (40 g: 0.2 mole) is dissolved in an aqueous caustic soda solution (2.5N). To this solution, cooled in an ice bath, is added 4-amino-5-chloro-2-methoxy benzoic acid (44.5 g) in solution in 300 ml of pyridine. Dicyclohexylcarbodiimide (85 g) is added in two portions. The mixture is vigorously stirred for 18 hours at ambient temperature. The medium is then diluted with 150 ml of water. Insoluble matter is removed by filtration and washed with water. The aqueous phase is brought to pH 10 by a 10N solution of caustic soda and extracted by chloroform. After drying (over Na$_2$SO$_4$) and evaporation of the organic phase, the residue is crystallised in isopropyl ether.

The solid thus obtained (56 g) is dissolved in 280 ml isopropyl alcohol and the solution acidified by 5N HCl. The hydrochloride which precipitates is recovered by filtration and recrystallised in 99% ethanol. The target product is obtained with a yield of 60%.

Melting point: 232°-234° C.

[alpha]$_D^{20}$ = -3.9° (c=1, H$_2$O).

COMPARISON EXAMPLE 1

R(+)-4-Amino-N-(3-quinuclidinyl)-5-chloro-2-methoxybenzamide hydrochloride (R(+)-4-Amino-N-(1-azabicyclo[2.2.2]oct-3-yl)-5-chloro-2-methoxybenzamide hydrochloride)

Following the procedure of Example 14 but using instead R(+)-3-aminoquinuclidine as prepared in Comparison Preparation 1 or 2, the corresponding R enantiomer is obtained.

Melting point: 233°-235° C.

[alpha]$_D^{20}$ = +3.8° (c=1, H$_2$O).

EXAMPLE 15

S(-)-4-Amino-N-(3-quinuclidinyl)-5-chloro-2-methoxybenzamide hydrochloride (S(-)-4-Amino-N-(1-azabicyclo[2.2.2]oct-3-yl)-5-chloro-2-methoxybenzamide hydrochloride)

S(-)-3-aminoquinuclidine (1.9 g) is dissolved in 33.5 ml of an aqueous 1 N caustic soda solution. To this solution is added drop by drop 4-acetamido-5-chloro-2-methoxybenzoyl chloride (3.75 g) in solution in 70 ml dioxane. After 15 minutes stirring, the reaction medium is acidified, washed with chloroform, basified with a concentrated aqueous caustic soda solution and the product extracted with chloroform. The organic phase is dried (over sodium sulphate) and then evaporated. The oily residue is dissolved in ethanol and ethanol/HCl is added to an acid pH. The 4-acetamido-5-chloro-2-methoxy-N-(3-quinuclidinyl)-benzamide hydrochloride so formed precipitates (quantitative yield) and is recovered by filtration.

The product is subsequently deacylated by refluxing for 30 minutes in a 5% solution of potassium hydroxide in ethanol. The reaction medium is then dissolved in water and extracted with chloroform. After drying and evaporation of the organic phase, the target hydrochloride is prepared and isolated as described in Example 14.

Melting point: 232°-234° C.

[alpha]$_D^{20}$ = -3.9° (c=1, H$_2$O).

COMPARISON EXAMPLE 2

R(+)-4-Amino-N-(3-quinuclidinyl)-5-chloro-2-methoxybenzamide dihydrochloride (R(+)-4-Amino-N-(1-azabicyclo2.2.2]oct-3-yl)-5-chloro-2-methoxybenzamide dihydrochloride)

Following the procedure of Example 15 but using instead R(+)-3-aminoquinuclidine as prepared in Comparison Preparation 1 or 2, the corresponding R enantiomer is obtained.

Melting point: 233°-235° C.

[alpha]$_D^{20}$ = +3.8° (c=1, H$_2$O).

EXAMPLE 16

S(-)-N-(3-quinuclidinyl)benzamide hydrochloride (S(-)-N-(1-azabicyclo2 2.2]oct-3-yl)benzamide hydrochloride)

Following the procedure of Example 14 but using benzoic acid in place of the 4-amino-5-chloro-2-methoxybenzoic acid, the title compound was prepared.

Melting point: 245° C.

[alpha]$_D^{20}$ = -17.8(1, CH$_3$OH).

EXAMPLE 17

S(-)-N-(3-quinuclidinyl)benzamide hydrochloride (S(-)-N-(1-azabicyclo[2.2.2]oct-3-yl)benzamide hydrochloride)

Following the procedure of Example 15 but using benzoyl chloride in place of the 4-amino-5-chloro-2-methoxybenzoyl chloride, the title compound was prepared.

Melting point: 245° C.

[alpha]$_D^{20}$ = -17.8(1, CH$_3$OH).

EXAMPLE 18

S(-)-3-chloro-N-(3-quinuclidinyl)benzamide hydrochloride (S(-)-N-(1-azabicyclo2.2.2]oct-3-yl)-3-chlorobenzamide hydrochloride)

Following the procedure of Example 14 but using 3-chlorobenzoic acid in place of the 4-amino-5-chloro-2-methoxybenzoic acid, the title compound was prepared.
Melting point: 244° C.
$[alpha]_D^{20} = -16.9$ (1, CH$_3$OH).

EXAMPLE 19

S(-)-3-chloro-N-(3-quinuclidinyl)benzamide hydrochloride (S(-)-N-(1-azabicyclo[2.2.2]oct-3-yl)-3-chlorobenzamide hydrochloride)

Following the procedure of Example 15 but using 3-chlorobenzoyl chloride in place of the 4-amino-5-chloro-2-methoxybenzoyl chloride, the title compound was prepared.
Melting point: 244° C.
$[alpha]_D^{20} = -16.9$ (1, CH$_3$OH).

EXAMPLE 20

S(-)-4-chloro-N-(3-quinuclidinyl)benzamide hydrochloride (S(-)-N-(1-azabicyclo[2.2.2]oct-3-yl)-4-chlorobenzamide hydrochloride)

Following the procedure of Example 14 but using 4-chlorobenzoic acid in place of the 4-amino-5-chloro-2-methoxybenzoic acid, the title compound was prepared.
Melting point: >260° C.
$[alpha]_D^{20} = -12.5$ (1, CH$_3$OH).

EXAMPLE 21

S(-)-4-chloro-N-(3-quinuclidinyl)benzamide hydrochloride (S(-)-N-(1-azabicyclo[2.2.21oct-3-yl)-4-chlorobenzamide hydrochloride)

Following the procedure of Example 15 but using 4-chlorobenzoyl chloride in place of the 4-amino-5-chloro-2-methoxybenzoyl chloride, the title compound was prepared.
Melting point: >260° C. $[alpha]_D^{20} = -12.5$ (1, CH$_3$OH).

EXAMPLE 22

S(-)-3,5-dichloro-N-(3-quinuclidinyl)benzamide hydrochloride (S(-)-N-(1-azabicyclo[2.2.2]oct-3-yl)-3,5-dichlorobenzamide hydrochloride)

Following the procedure of Example 14 but using 3,5-dichlorobenzoic acid in place of the 4-amino-5-chloro-2-methoxybenzoic acid, the title compound was prepared.
Melting point: >260° C.
$[alpha]_D^{20} = -14.1$ (1, CH$_3$OH).

EXAMPLE 23

S(-)-3,5-dichloro-N-(3-quinuclidinyl)benzamide hydrochloride (S(-)-N-(1-azabicyclo2.2.2]oct-3-yl)-3,5-dichlorobenzamide hydrochloride)

Following the procedure of Example 15 but using 3,5-dichlorobenzoyl chloride in place of the 4-amino-5-chloro-2-methoxybenzoyl chloride, the title compound was prepared.
Melting point: >260° C.
$[alpha]_D^{20} = -14.1$ (1, CH$_3$OH).

PHARMACOLOGY EXAMPLE

The dopamine hypothesis of schizophrenia attributes some of the symptoms of this illness to a raised mesolimbic dopamine function. In order to mimic the discrete nature of this disturbance, stereotaxic surgery was used to aim dopamine or amphetamine at a discrete mesolimbic nucleus. Male Sprague-Dawley (CD, Bradford strain) rats (250–300 g) were subject to standard stereotaxic techniques for the implantation of chronically indwelling bilateral guide cannulae for subsequent injections at the centre of the nucleus accumbens (Ant. 9.4, Vert. 0.0, Lat. ±1.6, atlas of De Groot). Rats were used 14 days after surgery, and on one occasion only.

Ability of known antischizophrenic agents to antagonise hyperactivity caused by intra-accumbens amphetamine was established using fluphenazine and sulpiride. These agents, the compound of Comparison Example 1, the compound of Example 14 and a racemic mixture of the compounds of Comparison Example 1 and Example 14 were prepared in distilled water for bilateral injection into the nucleus accumbens (1 ul over 5 s, with a further 55 s for deposition, rats manually restrained) 30 min before (+)amphetamine was also administered bilaterally into the nucleus accumbens, in a dose of 10 ug. This dose of amphetamine was shown in preliminary experiments to give a marked but submaximal hyperactivity response with an onset apparent within 5 min of injection, maximum intensity obtained 20–40 min after injection, and with a duration of 85–100 min.

Immediately after amphetamine injection, rats were placed in individual, screened perspex cages (25×15×15 cm high), each fitted with one photocell unit placed off centre, and hyperactivity measured as the numbers of interruptions of the photocell beams per 5 min. Rats were also visually observed to eliminate any non-specific effects (e.g. grooming, stereotypies) which may interfere with the measurement of locomotor activity. Experiments were carried out between 08.00am and 12.00am.

Figure 2:
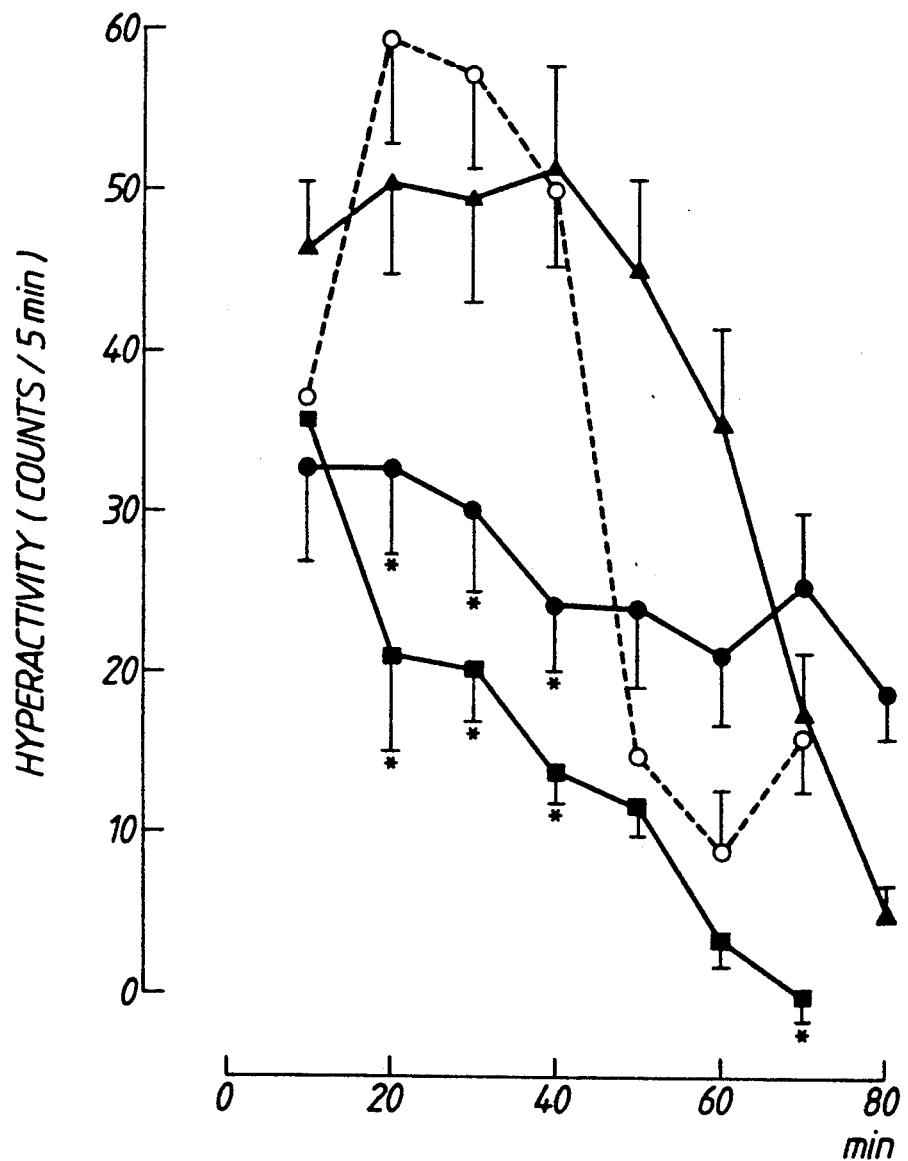

The results are shown with reference to the drawings, in which:

FIG. 1 shows the abilities of bilateral intraaccumbens fluphenazine and (-) sulpiride, (solid circles, ng doses indicated) to antagonise the hyperactivity caused by intra-accumbens amphetamine (10 μg bilateral, open circles, amphetamine response, plus vehicle for 'neuroleptic'); the potential antagonists were given 30 min before amphetamine; n=5-10; S.E.M.s <12.6%; significant reduction in the amphetamine response is indicated as *$P<0.01$ - $P<0.001$ (two-way ANOVA with Dunnett's test); and FIG. 2 shows the abilities of bilateral intraaccumbens Example 14 compound (S isomer), solid squares, Comparison Example 1 compound (R isomer) solid triangles and racemate (solid circles), each given at a dose of 10 ng, to antagonise the hyperactivity caused by intra-accumbens amphetamine (10 μg bilateral, open circles, amphetamine response, plus vehicle for compounds under test; the compounds under test were given 30 min before amphetamine; n=5. S.E.M.s given; significant reduction in the amphetamine response is indicated as *P<0.001 (two-way ANOVA with Dunnett's test).

Intra-accumbens fluphenazine (0.5-10 ng) and (-)sulpiride (0.1-1.25 ng) were shown to dose-dependently antagonise the hyperactivity development to a subsequent intra-accumbens injection of 10 ug amphetamine (FIG. 1). At 10 ng the compound of Comparison Example 1 (R isomer) failed to modify the amphetamine hyperactivity, but this was completely antagonised by the compound of Example 14 (S isomer) (FIG. 2). The antagonistic action of the racemate, at the same dose of 10 ng, fell between that of its two isomers, although significant antagonism was clear (FIG. 2).

In conclusion, in a test system which is sensitive to the antagonistic actions of known antipsychotic agents, at a fixed dose the R isomer (Comparison Example 1) is shown to be without effect whilst the S isomer (Example 14) caused maximum antagonism. The antagonistic action of the racemate, whilst significant, was less than that achieved by the same dose of its S isomer.

Pharmaceutical Methods and Compositions

Generally, schizophrenia and/or psychosis can be treated by means of this invention by administering internally to warm blooded animals including human beings certain S(-)-N-(1-azabicyclo[2.2.2]oct-3-yl)benzamides and thiobenzamides of Formula I, preferably Formula Ic, or a non-toxic organic or inorganic acid addition salt thereof in a wide variety of pharmaceutical forms well known in the art, preferably with a non-toxic pharmaceutical carrier such as is described below in an antischizophrenic and/or antipsychotic amount.

The active agent is administering orally, subcutaneously, intravenously or intramuscularly or parenterally and, if necessary, in repeated doses until satisfactory response is obtained. The daily dosage is from about 0.2 mcg to about 10 mg of active medication, advantageously from about 1 mcg to 1.0 mg.

The compositions may contain 0.2 mcg to 10 mg active medicament per unit dose. Preferably, the compositions contain from about 1 mcg to 10 mg of medicament, advantageously from about 1 mcg to about 1.0 mg per unit dose. The compounds may thus be presented in a therapeutic composition suitable for oral, parenteral, subcutaneous, intramuscular, intraperitoneal or intravenous administration. Thus, for example oral administration can take the form of elixirs, capsules, tablets or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone.

For parenteral administration, the carrier or excipient can be comprised of a sterile parenterally acceptable liquid; e.g., water or arachis oil contained in ampoules.

The pharmaceutical compositions may be formulated to contain from about 0.2 mcg/ml to about 10.0 mg/ml, preferably 10 mcg/ml or less. It is only necessary that the active ingredient of Formula I constitute an effective amount. In all of the above, it is only necessary that a suitable effective dosage will be consistent with the dosage form employed. The exact individual dosages, as well as daily dosages, will of course be determined according to standard medical principles under the direction of a physician or veterinarian.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention, and it is therefore understood that the invention is to be limited only by the scope of the appended claims.

What is claimed is:

1. A method for treating or preventing schizophrenia and/or psychosis, the method comprising the administration to a mammal in need of antischizophrenic and/or antipsychotic treatment an effective amount of a compound of general formula I

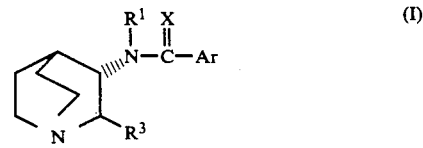

wherein:
X represents oxygen or sulphur;
each of $R^1$ and $R^3$ independently represents hydrogen or a $C_4$-$C_4$ alkyl group;
Ar represents
a phenyl ring optionally substituted by one, two or three $C_1$-$C_4$ alkoxy groups and/or by one or two halogen atoms; a phenyl ring of the general formula

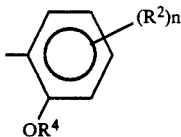

wherein $R^2$ represents halogen, 4-5-benzo, $C_1$-$C_8$ alkoxy, $C_1$-$C_4$ alkylcarbonyl or Am, wherein Am represents amino, methylamino or dimethylamino, $R^4$ represents $C_1$-$C_8$ alkyl,
n is 1 or 2; or
a pyrimidinyl moiety of the general formula

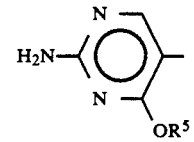

wherein $R_5$ is $C_1$-$C_4$ alkyl;
or an N-oxide and/or pharmaceutically acceptable salt thereof.

2. A method as claimed in claim 1, wherein each of $R^1$ and $R^3$ independently represents hydrogen, methyl or ethyl.

3. A method as claimed in claim 1 or 2, wherein Ar represents 4-Am-5-chloro-2-methoxyphenyl.

4. A method of treating or preventing schizophrenia and/or psychosis, the method comprising the administration to a mammal in need of antischizophrenic and/or antipsychotic treatment an effective amount of S(-)-4-amino-N-(1-azabicyclo[2.2.2]oct-3-yl)-5-chloro-2-methoxybenzamide or a salt thereof.

* * * * *